(12) United States Patent
Kim et al.

(10) Patent No.: US 10,307,737 B2
(45) Date of Patent: Jun. 4, 2019

(54) TRANSITION METAL-NOBLE METAL COMPLEX OXIDE CATALYST FOR DEHYDROGENATION PREPARED BY ONE-POT SYNTHESIS AND USE THEREOF

(71) Applicants: SK INNOVATION CO., LTD., Seoul (KR); KOREA ADVANCED INSTITUTE OF SCIENCE AND TECHNOLOGY, Daejeon (KR)

(72) Inventors: Tae Jin Kim, Seoul (KR); Chang Q Lee, Daejeon (KR); Young Eun Cheon, Daejeon (KR); Ju Hwan Im, Daejeon (KR); Min Kee Choi, Daejeon (KR)

(73) Assignees: SK INNOVATION CO., LTD., Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/339,082

(22) Filed: Oct. 31, 2016

(65) Prior Publication Data
US 2017/0120222 A1   May 4, 2017

(30) Foreign Application Priority Data

Nov. 3, 2015 (KR) .......................... 10-2015-0154081
Oct. 10, 2016 (KR) .......................... 10-2016-0130589

(51) Int. Cl.
*B01J 23/40* (2006.01)
*B01J 23/48* (2006.01)
(Continued)

(52) U.S. Cl.
CPC .............. *B01J 23/63* (2013.01); *B01J 21/04* (2013.01); *B01J 23/62* (2013.01); *B01J 35/0006* (2013.01);
(Continued)

(58) Field of Classification Search
CPC . B01J 37/04; B01J 21/04; B01J 21/066; B01J 23/40; B01J 23/48; B01J 23/62;
(Continued)

(56) References Cited

U.S. PATENT DOCUMENTS

| | | | |
|---|---|---|---|
| 4,374,046 A * | 2/1983 | Antos | ................. B01J 23/8953 502/327 |
| 7,304,012 B2 * | 12/2007 | Green | ..................... B01J 23/22 502/180 |

(Continued)

FOREIGN PATENT DOCUMENTS

JP            101477413        12/2014

OTHER PUBLICATIONS

Sattler, et al., "Platinum-Promoted Ga/Al2O3 as Highly Active, Selective, and Stable Catalyst for the Dehydrogenation of Propane**," Angew. Chem., 126:9405-9410 (2004).

(Continued)

*Primary Examiner* — Patricia L. Hailey
(74) *Attorney, Agent, or Firm* — Abelman, Frayne & Schwab

(57) ABSTRACT

Disclosed are a complex oxide catalyst for dehydrogenation, a method of preparing the same, and use thereof, wherein the catalyst includes a first transition metal selected from the group consisting of gallium, vanadium, chromium, manganese, molybdenum, and zinc, a hydrogen-activating metal including at least one selected from the group consisting of Groups 8, 9, 10, and 11 elements in a periodic table, and alumina, the amount of the first transition metal being 0.1 wt % to 20 wt %, the amount of the hydrogen-activating metal being 0.01 wt % to 2 wt %, based on the amount of the alumina, the first transition metal being loaded on the alumina, and the hydrogen-activating metal being surrounded by the alumina.

11 Claims, 4 Drawing Sheets

(51) Int. Cl.
    *B01J 23/63*     (2006.01)
    *B01J 23/62*     (2006.01)
    *B01J 21/04*     (2006.01)
    *B01J 35/00*     (2006.01)
    *B01J 37/04*     (2006.01)
    *B01J 37/02*     (2006.01)
    *B01J 37/08*     (2006.01)
    *C07C 5/48*     (2006.01)

(52) U.S. Cl.
CPC ........... B01J 37/0211 (2013.01); B01J 37/04 (2013.01); B01J 37/08 (2013.01); C07C 5/48 (2013.01); *C07C 2521/04* (2013.01); *C07C 2523/08* (2013.01); *C07C 2523/42* (2013.01); *C07C 2523/62* (2013.01); *C07C 2523/63* (2013.01)

(58) Field of Classification Search
CPC ... B01J 23/63; B01J 23/70; B01J 23/89; B01J 37/08; B01J 37/0211
USPC .................................. 502/312–314, 317–339
See application file for complete search history.

(56) References Cited

U.S. PATENT DOCUMENTS

2004/0127352 A1* 7/2004 Jin ........................... B01J 21/04
                                                                          502/332
2013/0178692 A1   7/2013  Luo et al.

OTHER PUBLICATIONS

Sattler, et al., Supporting Information—"Platinum-Promoted Ga/Al2O3 as Highly Active, Selective, and Stable Catalyst for the Dehydrogenation of Propane**," Angew. Chem., 126:9405-9410 (2004).

* cited by examiner

… (US 10,307,737 B2)

TRANSITION METAL-NOBLE METAL COMPLEX OXIDE CATALYST FOR DEHYDROGENATION PREPARED BY ONE-POT SYNTHESIS AND USE THEREOF

CROSS-REFERENCE TO RELATED APPLICATION

This application claims the benefit of Korean Patent Application Nos. 10-2015-0154081, filed Nov. 3, 2015, and 10-2016-0130589, filed Oct. 10, 2016, entitled "Transition Metal-Noble Metal Complex Oxide Catalysts Prepared by One-Pot for Dehydrogenation and Use Thereof" which is hereby incorporated by reference in its entirety into this application.

BACKGROUND OF THE INVENTION

1. Technical Field

The present invention relates to a transition metal-noble metal complex oxide catalyst for dehydrogenation, prepared by one-pot synthesis, and to the use thereof.

2. Description of the Related Art

These days, as the production of shale gas containing a large amount of gas such as methane or ethane is drastically increasing, the profitability of a naphtha cracker is decreased and the profitability of an ethane cracker is remarkably increased. Thus, the production of olefins, such as propylene or butylene, as byproducts of the naphtha cracker is greatly reduced. The demand for olefin having a small number of carbon atoms is continuously increasing and the supply of olefin is gradually decreasing. Hence, thorough research is ongoing into propane and butane dehydrogenation processes for directly producing olefin from propane or butane having a small number of carbon atoms.

Examples of a typical catalyst for dehydrogenation of propane and butane may include a Pt—Sn/$Al_2O_3$ catalyst (Oleflex process) and a chromia-alumina catalyst (Catofin process), which are already utilized in commercial processes because they have high olefin selectivity and coke stability. However, the Pt—Sn/$Al_2O_3$ catalyst is problematic upon repeated catalyst regeneration because the concentration of Sn(0) on the surface of Pt is continuously increased and thus the activity of the catalyst is decreased and Pt sintering may undesirably occur, and hence, an oxychlorination process must be performed during catalyst regeneration in commercial processes. The chromia-alumina catalyst suffers from decreased catalytic activity due to sintering of alumina and movement of $Cr^{3+}$ upon repeated catalyst regeneration.

With the goal of solving the deactivation of the Pt—Sn/$Al_2O_3$ catalyst, the preparation of a Pt—Sn—M/$Al_2O_3$-based catalyst by adding the above catalyst with a metal M, such as zinc, lanthanum, lithium, sodium, potassium, or rubidium, has been reported (KR 1,477,413 B1). This catalyst is composed essentially of Pt and Sn, as in conventional cases. In particular, Pt functions as an active component directly participating in dehydrogenation, and the newly added metal M plays an auxiliary role in decreasing the extent of deactivation of Pt and thus the function thereof is limited to dehydrogenation. The Pt—Sn—M/$Al_2O_3$-based catalyst is merely a simple extension of the conventional Pt—Sn/$Al_2O_3$ catalyst. Furthermore, the Pt—Sn—M/$Al_2O_3$-based catalyst requires plurality of metal component impregnation processes, undesirably incurring complicated processing and negating economic benefits.

In order to overcome the limitations of conventional catalysts for the dehydrogenation of propane or butane, a catalyst configured such that Ga and a small amount (0.1 wt %) of Pt are loaded on alumina has been reported in the literature (J. J. H. B. Sattler et al., Angew. Chem., 126:9405, 2014 and US 2013/0178682 A1). This publication proposed gallium oxide as the main active site and reported that Pt aids re-coupling of hydrogen to thus increase reactivity. The corresponding catalyst exhibited early propane conversion of about 46%, but the propane conversion was remarkably decreased to about 30%, corresponding to 60% of the early propane conversion, within 48 hr, and was then maintained at about 30% for 15 days. Based on the results of chemisorption of carbon monoxide (CO), the Pt dispersion was considerably decreased, from 20% to less than 5%, after thermal treatment. Hence, in the dehydrogenation of olefin, it is very difficult to retain the high Pt dispersion under catalyst regeneration conditions of 750° C. and air, and the effective suppression of Pt sintering is regarded as very important in terms of maintaining the early conversion of the catalyst.

SUMMARY OF THE INVENTION

Accordingly, the present invention has been made keeping in mind the problems encountered in the related art, and embodiments of the present invention are intended to provide a complex oxide catalyst for dehydrogenation, a method of preparing the same, and use thereof, in which the catalyst is prepared by mixing individual precursors of a first transition metal as an active metal and a hydrogen-activating metal and a second transition metal as adjuvant metals with an alumina precursor and performing one-pot synthesis, and thus has activity different from that of conventional catalysts.

A first aspect of the present invention provides a complex oxide catalyst for dehydrogenation, comprising: a that transition metal selected from the group consisting of gallium, vanadium, chromium, manganese, molybdenum, and zinc, a hydrogen-activating metal comprising at least one selected from the group consisting of Groups 8, 9, 10, and 11 elements in a periodic table, and alumina, wherein the amount of the first transition metal is 0.1 wt % to 20 wt % and the amount of the hydrogen-activating metal is 0.01 wt % to 2 wt %, based on the amount of alumina, the first transition metal is loaded on the alumina, and the hydrogen-activating metal is surrounded by the alumina.

In an exemplary embodiment, the catalyst fill/her includes a second transition metal selected from the group consisting of cerium and zirconium, the amount of the second transition metal may be 0.1 wt % to 20 wt % based on the amount of alumina, and the second transition metal may be loaded on the alumina.

In an exemplary embodiment, the hydrogen-activating metal may include at least one selected from the group consisting of Co, Ni, Cu, Ru, Rh, Pd, Ag, Ir, Pt and Au.

A second aspect of the present invention provides a method of preparing a complex oxide catalyst the dehydrogenation, comprising: providing a precursor of a first transition metal selected from the group consisting of gallium, vanadium, chromium, manganese, molybdenum, and zinc, providing a precursor of a hydrogen-activating metal comprising at least one selected from the group consisting of Groups 8, 9, 10, and 11 elements in the periodic table, providing an alumina precursor, mixing the precursor of the first transition metal, the precursor of the hydrogen-activating metal and the alumina precursor in one-pot, and synthesizing a catalyst from the mixture in one-pot using a sol-gel process, wherein the amount of the first transition metal is 0.1 wt % to 20 wt % and the amount of the hydrogen-activating metal is 0.01 wt % to 2 wt % based on the amount of alumina in the final catalyst.

In an exemplary embodiment, the method may further include providing a precursor of a second transition metal selected from the group consisting of cerium and zirconium, and mixing the precursor of the second transition metal in one-pot, wherein the amount of the second transition metal may be 0.1 wt % to 20 wt % based on the amount of alumina in the final catalyst.

In an exemplary embodiment, the method may further include impregnating a hydrogen-activating metal comprising at least one selected from the group consisting of Groups 8, 9, 10, and 11 elements in the periodic table, after synthesizing the catalyst using the sol-gel process, wherein the amount of the hydrogen-activating metal may be 0.01 wt % to 2 wt % based on the amount of alumina in the final catalyst.

In an exemplary embodiment, the method may further include impregnating a second transition metal selected from the group consisting of cerium and zirconium, wherein the amount of the second transition metal may be 0.1 wt % to 20 wt % based on the amount of alumina in the final catalyst.

In an exemplary embodiment, the method may further include drying and thermally treating the catalyst, after synthesizing the catalyst using the sol-gel process.

In an exemplary embodiment, the drying may be performed at a temperature of 50 to 200° C., and the thermally treating may be performed at a temperature of 350 to 1000° C.

In an exemplary embodiment, the hydrogen-activating metal may include at least one selected from the group consisting of Co, Ni, Cu, Ru, Rh, Pd, Ag, Ir, Pt and Au.

A third aspect of the present invention provides a method of preparing an olefin, comprising: providing a feed comprising at least one selected from the group consisting of methane, ethane, propane, butane, isobutane and cyclohexane, and dehydrogenating the feed using the catalyst according to the first aspect or the catalyst prepared by the method according to the second aspect.

In an exemplary embodiment, the dehydrogenating may be performed at a temperature of 300 to 800° C.

According to embodiments of the present invention, a dehydrogenation catalyst is configured such that a first transition metal, serving as an active component, and a hydrogen-activating metal and a second transition metal, serving as adjuvant components, are loaded on alumina. Thus, even when the catalyst undergoes frequent regeneration processes, the conversion, selectivity and catalytic durability in the dehydrogenation reaction can be maintained for a long time.

According to embodiments of the present invention, a method of preparing the dehydrogenation catalyst adopts a one-pot synthesis process and a sol-gel process of metal precursors and an alumina precursor, and thus, thermal drying and thermal sintering can be performed only once, thereby yielding a catalyst having high activity for dehydrogenation.

DESCRIPTION OF SPECIFIC EMBODIMENTS

Exemplary embodiments of the present invention may be understood through the following description. The following description should be understood to explain specific embodiments of the present invention, and the present invention is not necessarily limited thereto. Furthermore, the appended drawings are provided for clarity, and the present invention is not limited thereto, and details of the individual components thereof may be properly understood by the specific effects of the relevant description, which will be described later.

As used herein, the terms may be defined as follows.

The term "dehydrogenation" refers to a reaction for removing hydrogen from a compound.

The term "impregnation process" refers to the process of preparing a catalyst by impregnating a catalyst support, such as alumina, silica, or titania, having a large surface area, with a catalyst precursor solution, followed by drying and calcination. In particular, an incipient wetness impregnation process is widely useful, which is performed in a manner of using an impregnation solution in an amount corresponding to the porous volume of the catalyst support.

The term "sol-gel process" refers to the process of preparing a catalyst having high dispersion by dissolving a catalyst precursor in water or an organic solvent having a relatively high boiling point, followed by adding a support component thereto and slow hydrolysis.

The term "one-pot synthesis" means that when a target compound is synthesized through a reaction procedure comprising two or more steps, products of individual steps (intermediate products) are allowed to continuously react with the reactant of the next step in a single reactor without any purification thereof, thus obtaining a desired compound.

The term "complex oxide" refers to an oxide composed of two or more oxides.

Figure 1:
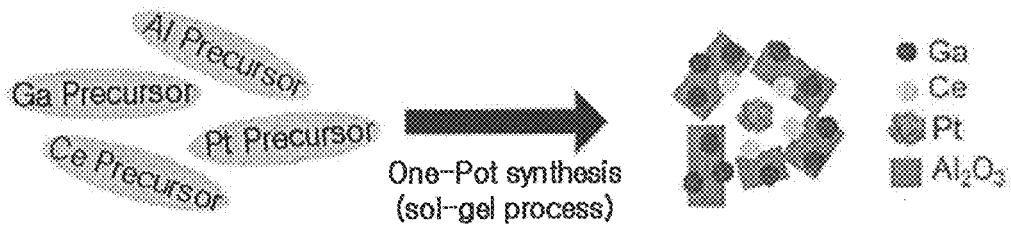
FIG. 1 shows a complex oxide catalyst prepared from a first transition metal precursor, a second transition metal precursor, a hydrogen-activating metal precursor, and an alumina precursor through one-pot synthesis using a sol-gel process, according to an embodiment of the present invention.

FIG. 1 shows a complex oxide catalyst, prepared from a precursor of a first transition metal such as gallium, a precursor of a second transition mewl such as cerium, a precursor of a hydrogen-activating metal such as platinum, and an alumina precursor through one-pot synthesis using a sol-gel process, according to an embodiment of the present invention.

As shown in FIG. 1, the complex oxide catalyst for dehydrogenation according to an embodiment of the present invention may be prepared from the first transition metal precursor, the hydrogen-activating metal precursor, the second transition metal precursor, and the alumina precursor through one-pot synthesis using a sol-gel process.

The first transition metal may be selected from, but is not limited to, the group consisting of gallium, vanadium, chromium, manganese, molybdenum, and zinc. The amount of the first transition metal is 0.1 to 20 wt %, particularly 0.5 to 10 wt %, and more particularly 1 to 5 wt %, based on the amount of alumina in the final catalyst. If the amount of the first transition metal is less than 0.1 wt %, the number of active sites is low and thus the activity of the catalyst may be too low. On the other hand, if the amount thereof exceeds 20 wt %, the active sites of the transition metal may not be effectively used.

The hydrogen-activating metal may include at least one selected from the group consisting of Groups 8, 9, 10 and 11 elements in the periodic table, particularly the group consisting of Co, Ni, Cu, Ru, Rh, Pd, Ag, Ir, Pt and Au, and more particularly the group consisting of Pt, Pd, and Ni. Most particularly useful is a noble metal such as Pt. The amount of the hydrogen-activating metal is 0.01 to 2 wt %, particularly 0.05 to 1 wt %, and more particularly 0.1 to 0.5 wt %, based on the amount of alumina in the final catalyst. If the amount of the hydrogen-activating metal is less than 0.01 wt %, the interaction with the first transition metal may become insufficient. On the other hand, if the amount thereof exceeds 2 wt %, the olefin selectivity of the catalyst may decrease, or the first transition metal oxide may be reduced, undesirably decreasing the number of active sites.

The second transition metal may be selected from the group consisting of, for example, Zr and lanthanide metals, and is particularly Zr or Ce, and more particularly Ce, but the present invention is not limited thereto. The amount of the second transition metal is 0.1 to 20 wt %, particularly 0.5 to 10 wt %, and more particularly 1 to 5 wt %, based on the amount of alumina in the final catalyst. If the amount of the second transition metal is less than 0.1 wt %, sintering of the hydrogen-activating metal cannot be suppressed. On the other hand, if the amount thereof exceeds 20 wt %, the second transition metal may not be effectively used.

Figure 6:
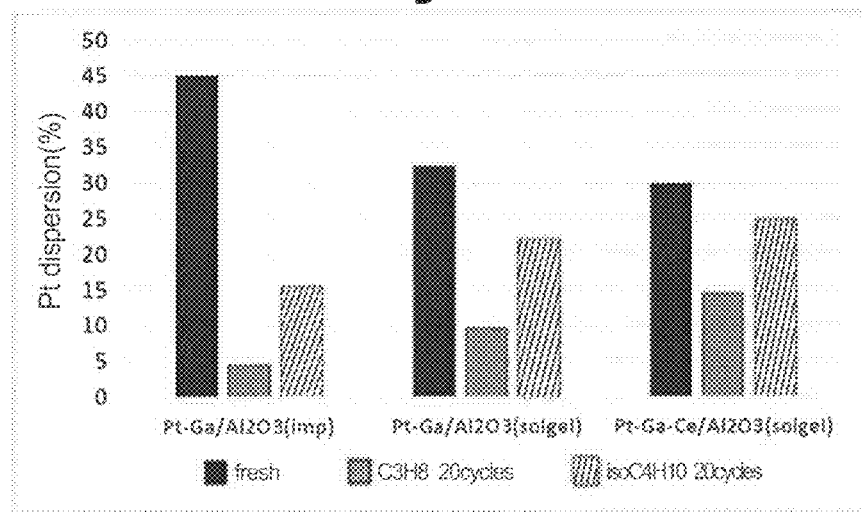
FIG. 6 is a graph showing the CO chemisorption amount of the catalyst in Example 3 of the present invention.
Figure 7:
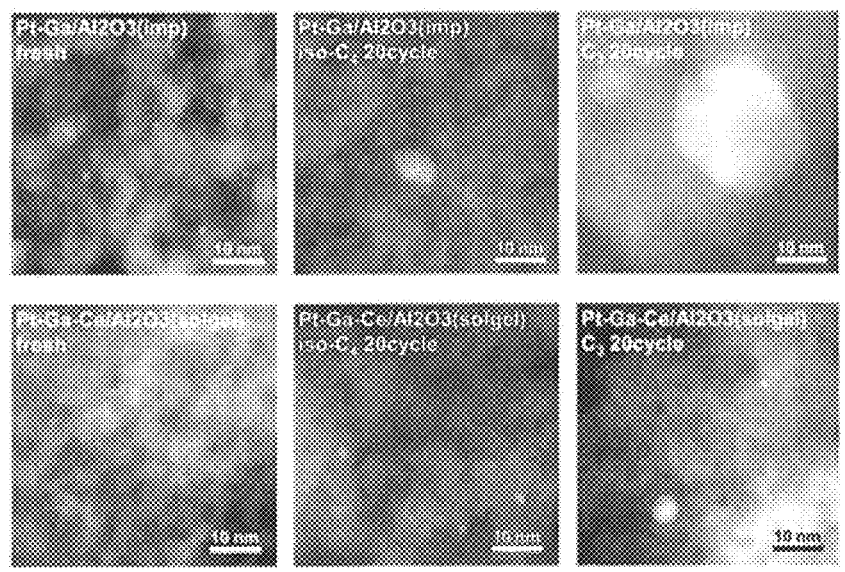
FIG. 7 shows transmission electron microscopy (TEM) images of the catalysts used for 20 cycles of propane and isobutane dehydrogenation and catalyst regeneration in Example 4 of the present invention.

With reference to FIG. 1 the hydrogen-activating metal, for example, a noble metal such as Pt, may be surrounded by alumina having the first transition metal and the second transition metal loaded thereon. FIGS. 6 and 7 respectively show the CO chemisorption amount and the TEM images of the sol-gel sample according to an embodiment of the present invention and the impregnation sample according to an comparative example. As shown in the TEM images, the samples obtained through the two synthesis methods have the same Pt size but the CO chemisorption amount is analyzed to be 30% lower in the sol-gel sample than in the impregnation sample. In this way, the surrounding of the hydrogen-activating metal (e.g. Pt) by the alumina having the first transition metal and the second transition metal loaded thereon is proven based on the results of CO chemisorption amount of FIG. 6 and the TEM of FIG. 7. When the hydrogen-activating metal is surrounded by the alumina, sintering due to coalescence between hydrogen-activating metal clusters may be effectively suppressed. Also, when the second transition metal is further added to the catalyst, it may chemically interact with the hydrogen-activating metal, thus effectively suppressing the sintering of the hydrogen-activating metal. In the case where not only the hydrogen-activating metal but also the first transition metal and the second transition metal are synthesized in a one-pot manner together with alumina using a sol-gel process, the dispersion of the first transition metal or the second transition metal in alumina is increased, whereby these active components may function effectively.

In a sol-gel synthesis process, a complex oxide catalyst comprising all of the first transition metal, the hydrogen-activating metal, and the second transition metal may be prepared in a manner such that respective precursors of alumina, the first transition metal, the hydrogen-activating metal, and the second transition metal are dissolved in a solvent (e.g. water), heated (e.g. to 358 K), stirred to hydrolyze the alumina precursor, and added with an acid (e.g. $HNO_3$) to peptize the alumina, after which the solvent is evaporated from the prepared solution, thus obtaining a sufficiently dried product, which is then dried and thermally treated, resulting in a catalyst. In an exemplary embodiment, drying may be performed at a temperature of 50 to 200° C. and thermal treatment may be carried out at a temperature of 350 to 1000° C.

Preparation of Catalyst

In an embodiment of the present invention, a complex oxide catalyst for dehydrogenation may be prepared by mixing alumina precursor with a precursor of the first transition metal selected from the group consisting of gallium, vanadium, chromium, manganese, molybdenum, and zinc and a precursor of a hydrogen-activating metal comprising at least one selected from the group consisting of Groups 8, 9, 10, and 11 elements in the periodic table, followed by one-pot synthesis using a sol-gel process. In another embodiment, a precursor of the second transition metal selected from the group consisting of cerium and zirconium is further mixed, followed by one-pot synthesis, resulting in a complex oxide catalyst for dehydrogenation. The mixing ratio of the precursors may be set based on the above description of the catalyst.

The alumina precursor may be selected from, but is not limited to, the group consisting of aluminum isopropoxide, aluminum nitrate nonahydrate, aluminum fluoride trihydrate, aluminum phosphate hydrate, and aluminum chloride hexahydrate.

As the precursors of metal components, any salt or complex of the corresponding metal that is known in the art may be used without limitation, so long as it may be subjected to sol-gel synthesis with the alumina precursor. In an exemplary embodiment, when Pt is used as the noble metal, it may be provided in the form of hydrides, fluorides (e.g. $PtF_6$, $PtF_4$, $[PtF_5]_4$ and the like), chlorides (e.g. $PtCl_3$, $PtCl_4$, $Pt_6Cl_{12}$ and the like), bromides ($PtBr_3$, $PtBr_4$ and the like), iodides (e.g. $PtI_2$, $PtI_3$, $PtI_4$ and the like), oxides (e.g. PfO, $PtO_2$ and the like), sulfides (e.g. PtS, $PtS_2$ and the like), carbonyls (e.g. $Pt(CO)_4$) and/or complexes (e.g. $[PtCl_2(NH_3)_2]$, $[PtCl^2(NH_3)_2]$, $K_2[PtCl_6]$, $K_2[Pt(CN)_4]$, $PtCl_4.5H_2O$, $K[PtCl_3(NH_3]$, $Na_2[PtBr_6]$—$6H_2O$, $(NH_4)_2[PtBr_6]$, $K_2[PtI_6]$, $(NH_4)_2[PtCl_6]$, $K_2[Pt(CN)_6]$, $(NH_4)_2[PtCl_4]$, $K_2[Pt(NO_2)_4]$, $K[PtCl_3(C_2H_4)]$—$H_2O$ $[Pt(NH_3)_4](NO_3)_2$, $H_2PtCl_6$ and the like), but the present invention is not necessarily limited thereto.

The sol-gel process is cared out in a manner in which a solution of a metal organic or inorganic compound is subjected to hydrolysis and polycondensation, and thus the sol is solidified into a gel, which is then heated, thus yielding an oxide. Such a sol-gel process may be largely classified into two types, depending on the manner in which gelation is performed. As one of the two types, a colloidal process is performed by dispersing the colloidal particles in the solution to form a feed solution, that is, a sol and then gelling the unstable sol. As the other of the two types, the sol is made using a metal organic compound such as an alkoxide as a starting material, and is then subjected to hydrolysis and polycondensation, thereby yielding a gel. In the present invention, any sol-gel process may be applied so long as it is typically useful from the standpoint of a person skilled in the art.

In the sol gel synthesis process, the complex oxide catalyst comprising all of the first transition metal, the hydrogen-activating metal, and the second transition metal may be prepared by dissolving respective precursors of alumina, the first transition metal, the noble metal, and the second transition metal in a solvent (e.g. water), followed by heating (e.g. to 358 K.), stirring to hydrolyze the alumina precursor, and addition of an acid (e.g. $HNO_3$) to peptize the alumina, after which the solvent is evaporated from the prepared solution, thus obtaining a sufficiently dried product, which is then dried and thermally treated, resulting in a catalyst.

In an embodiment of the present invention, drying and thermally treating the synthesized catalyst may be further performed, after synthesis of the catalyst using the sol-gel process.

Drying is performed to remove the remaining water from the formed gel, and the drying temperature and drying time may be set depending on the typical water drying conditions. For example, the drying temperature may range from 50 to 200° C., and particularly from 70 to 120° C., and the drying time may range from 3 to 24 hr, and particularly from 6 to 12 hr.

Thermal treatment is performed to form metal-alumina at a temperature of 350 to 1000° C., and particularly 500 to 800° C., for 1 to 12 hr, and particularly 3 to 6 hr. If the thermal treatment temperature is lower than 350° C. or the thermal treatment time is shorter than 1 hr, metal-alumina is not sufficiently formed. On the other hand, if the thermal treatment temperature exceeds 1000° C. or the thermal treatment time exceeds 12 hr, the metal-alumina phase may be degraded.

Use

In embodiments of the present invention, the complex oxide catalyst may be applied to a variety of dehydrogenation processes, and may exhibit improved activity. Examples of the dehydrogenation process may include, but are not limited to, converting methane into olefin, converting propane into propylene, converting butane into butene or butadiene, and converting cyclohexane into benzene.

When the reactant (e.g. methane, ethane, propane, butane, isobutane, cyclohexane, or mixtures thereof) is fed into a reactor, the amount of introduced reactant may be adjusted using a mass flow rate controller. Particularly, the amount of the catalyst is set so that the WHSV (Weight Hourly Space Velocity) is 0.5 to $100^{-1}$, particularly 1 to 50 $hr^{-1}$, and more particularly 2 to 25 $hr^{-1}$, based on the total amount of the reactant. If the space velocity is less than 0.5 $hr^{-1}$, the amount of produced olefin is too small. On the other hand, if the space velocity exceeds 100 $hr^{-1}$, coking may rapidly occur due to the reaction byproducts of the catalyst.

The reaction temperature for direct dehydrogenation of the reactant is set to the range of 300 to 800° C., and particularly 500 to 700° C. For propane dehydrogenation, the reaction temperature may be maintained at 620° C., and for butane dehydrogenation, the reaction temperature may be maintained at 550° C. If the reaction temperature is lower than 300° C., the reaction of the reactant is not sufficiently activated. On the other hand, if the reaction temperature is higher than 800° C., decomposition of the reactant, for example, butane, may mainly occur, which is undesirable.

A better understanding of the present invention may be obtained through the following examples which are set forth to illustrate, but are not to be construed to limit the present invention.

Preparation Example 1

One-Pot Preparation of First Transition Metal-Noble Metal-Alumina Complex Catalyst Using Sol-Gel Process In an embodiment, a complex catalyst may be prepared from a first transition metal precursor, a noble metal precursor, and an alumina precursor by one-pot synthesis using a sol-gel process.

In an exemplary embodiment, a $Pt$—$Ca/Al_2O_3$ complex catalyst may be synthesized. Tetraamineplatinum nitrate ($Pt(NH_3)_4(NO_3)_2$), gallium nitrate ($Ga(NO_3)_3$), and aluminum isopropoxide ($C_9H_{21}AlO_3$) were used as precursors of platinum, gallium, and alumina, respectively. About 0.04 g of tetraamineplatinum nitrate and about 2.27 g of gallium nitrate were added to about 700 mL of distilled water so that respective amounts of Pt and Ga were about 0.1 wt % and about 3 wt % based on the amount of alumina in the final catalyst, thus affording an aqueous solution, which was then stirred at about 358 K. The aqueous solution in which Pt and Ga precursors were completely dissolved was added with about 80.1 g of aluminum isopropoxide, and was then further stirred at about 358 K. for about 30 min. The solution in which aluminum isopropoxide was hydrolyzed was added with about 8.1 g of nitric acid ($HNO_3$, about 61% solution) and thus peptized, and the synthesized solution was continuously stirred for about 12 hr until the distilled water was completely evaporated, thus obtaining a sufficiently dried product, which was then fired at about 1023 K for about 2 hr in dry air. The prepared catalyst is represented by "Pt—$Ga/Al_2O_3$ (sol-gel)".

Preparation Example 2

One-Pot Preparation of First Transition Metal-Noble Metal-Second Transition Metal-Alumina Alumina Complex Catalyst Using Sol-Gel Process In an embodiment, a second transition metal may be selected from the group consisting of cerium and zirconium. In an exemplary embodiment, cerium nitrate ($Ce(NO_3)_3$) was used as a cerium precursor, and about 0.04 g of tetraamineplatinum nitrate, about 2.27 g of gallium nitrate and about 0.62 g cerium nitrate were added to about 700 mL of distilled water so that respective amounts of Pt, Ga and Ce were about 0.1 wt %, about 3 wt % and about 1 wt % based on the amount of alumina in the final catalyst, thus affording an aqueous solution that was then processed in the same manner as in Preparation Example 1, thus preparing a catalyst, which was then thermally treated. The resulting catalyst is represented by "Pt—Ga—$Ce/Al_2O_3$ (sol-gel)". In the Preparation Example of the present invention, all catalyst components are mixed together and synthesized in a one-pot manner, and thus thermal drying and thermal treatment are perforated only once.

Preparation Example 3

One-Pot Preparation of 1 wt % Pt—Ga—$Ce/Al_2O_3$ Complex Catalyst Using Sol-Gel Process In an embodiment, a complex catalyst may be prepared from a lint transition metal precursor, a noble metal precursor, a second transition metal precursor and an alumina precursor through one-pot synthesis using a sol-gel process.

In an exemplary embodiment, a 1 wt % Pt—Ga—Ce/Al$_2$O$_3$ complex catalyst may be synthesized. Gallium nitrate (Ga ((NO$_3$)$_3$), tetraamineplatinum nitrate, cerium nitrate and aluminum isopropoxide (C$_9$H$_{21}$Al$_3$)$_3$) were used as precursors of Ga, Pt, Co and alumina, respectively. About 0.4 g of tetraamineplatinum nitrate, about 2.27 g of gallium nitrate and 0.62 g of cerium nitrate were added to about 700 mL of distilled water so that respective amounts of Pt, Ga and Ce were about 1 wt %, about 3 wt % and about 1 wt % based on the amount of alumina in the final catalyst, thus affording an aqueous solution that was then processed in the same manner as in Preparation Example 1, thus preparing a catalyst, which was then thermally treated. The resulting catalyst is represented by "1 wt % Pt—Ga—Ce/Al$_2$O$_3$ (sol-gel)".

Comparative Preparation Example 1

One-Pot Preparation of First Transition Metal-Alumina Complex Catalyst Using Sol-Gel Process In a comparative embodiment, a complex catalyst may be prepared form a first transition metal precursor and an alumina precursor through one-pot synthesis using a sol-gel process. In an exemplary comparative embodiment, a Ga/Al$_2$O$_3$ complex catalyst may be synthesized. Gallium nitrate (Ga(NO$_3$)$_3$) and aluminum isopropoxide (C$_9$H$_{21}$AlO$_3$) were used as precursors of gallium and alumina, respectively. About 2.27 g of gallium nitrate was added to about 700 mL of distilled water so that the amount of Ga was about 3 wt % based on the amount of alumina in the final catalyst, tints affording an aqueous solution, which was then stirred at about 358 K. The aqueous solution in which the Ga precursor was completely dissolved was added with about 80.1 g of aluminum isopropoxide, and then further stirred at about 358 K for about 30 min. The solution in which aluminum isopropoxide was hydrolyzed was added with about 8.1 g of nitric acid (HNO$_3$, about 61% solution), and thus peptized, and the synthesized solution was continuously stirred for about 12 hr until the distilled water was completely evaporated, thus obtaining a sufficiently dried product, which was then fired a about 1023 K for about 2 hr in dry air. The prepared catalyst is represented by "Ga/Al$_2$O$_3$ (sol-gel)".

Comparative Preparation Example 2

Synthesis of Pt—Ga/Al$_2$O$_3$ Complex Catalyst Using Incipient Wetness Impregnation Tetraamineplatinum nitrate (Pt(NH$_3$)$_4$(NO$_3$)$_2$) and gallium nitrate (Ga(NO$_3$)$_3$) were used as precursors of Pt and Ga, respectively. Tetraamineplatinum nitrate and gallium nitrate were loaded on commercially available alumina (gamma-alumina, STREM CHEMICALS) using an incipient wetness impregnation process so that respective amounts of Pt and Ga were about 0.1 wt % and about 3 wt % based on the amount of alumina in the final catalyst. The impregnated alumina was dried at about 373 K for about 24 hr, and fired at about 1023 K for about 2 hr in dry air. The prepared catalyst is represented by "Pt—Ga/Al$_2$O$_3$ (imp)".

Comparative Preparation Example 3

Synthesis of Pt—Ga—Ce/Al$_2$O$_3$ Complex Catalyst Using Incipient Wetness Impregnation Tetraamineplatinum nitrate, gallium nitrate and cerium nitrate were loaded on commercially available alumina using an incipient wetness impregnation process in the same manner as in Comparative Preparation Example 2 so that respective amounts of Pt, Ga and Ce were about 0.1 wt %, about 3 wt % and about 1 wt % based on the amount of alumina in the final catalyst, followed by thermal treatment under the same conditions. The obtained catalyst is represented by "Pt—Ga—Ce/Al$_2$O$_3$ (imp)". In Comparative Preparation Example 3, thermal drying and thermal treatment are performed at least three times.

Example 1

Measurement of Propane Dehydrogenation Reactivity

The synthesized samples, namely Pt—Ga/Al$_2$O$_3$ (imp), Pt—Ga—Ce/Al$_2$O$_3$ (imp), Pt—Ga/Al$_2$O$_3$ (sol-gel), Pt—Ga—Ce/Al$_2$O$_3$ (sol-gel), Ga/Al$_2$O$_3$ (sol-gel), and 1 wt % Pt—Ga—Ce/Al$_2$O$_3$ (sol-gel) in which the amount of Pt was increased to 1 wt %, were subjected to propane dehydrogenation/catalyst regeneration cycling.

Before the propane dehydrogenation, to minimize the effects of heat and material transfer, each sample was formed to a size of about 75 to about 100 meshes, and was used as a final catalyst for the reaction. The reaction was carried out using about 0.6 g of the catalyst in a fixed-bed continuous flow reactor, and all the samples were treated in-situ under conditions of about 893 K and a He flow rate of about 200 sccm, before the reaction. Propane dehydrogenation was carried out under operating conditions of WHSV=5.4$^{-1}$, 893 K, P$_{He}$=80 kPa, and P$_{propane}$=20 kPa. The reaction was carried out for about 1 hr, followed by catalyst regeneration and then the reaction again. Specifically, reaction/catalyst regeneration cycling was performed as follows:

(i) performing primary propane dehydrogenation at about 893 K for about 1 hr;

(ii) allowing helium to flow at about 893 K for about 30 min;

(iii) regenerating the catalyst in dry air at about 893 K for about 30 min;

(iv) allowing helium to flow at about 893 K for about 30 min; and (v) performing secondary propane dehydrogenation at about 893 K.

Figure 2:
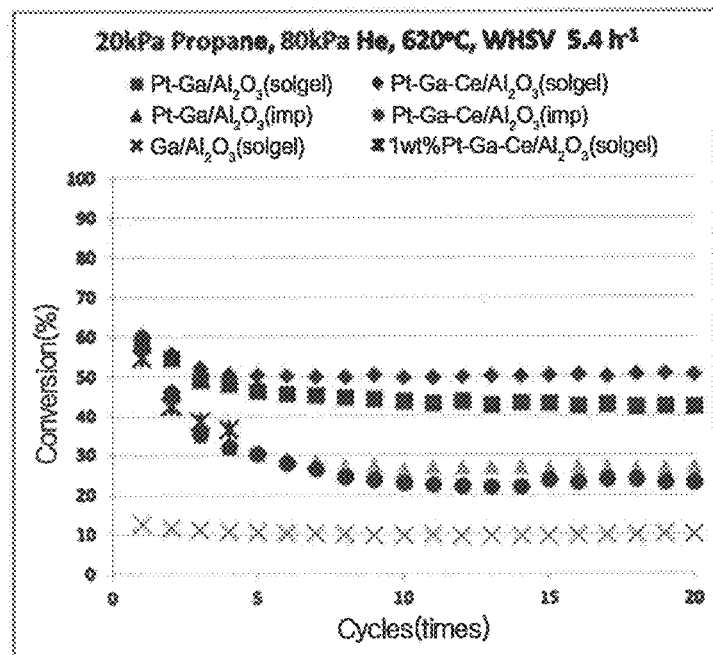
FIG. 2 is a graph showing the propane conversion during 20 cycles of propane dehydrogenation and catalyst regeneration in Example 1 of the present invention.
Figure 3:
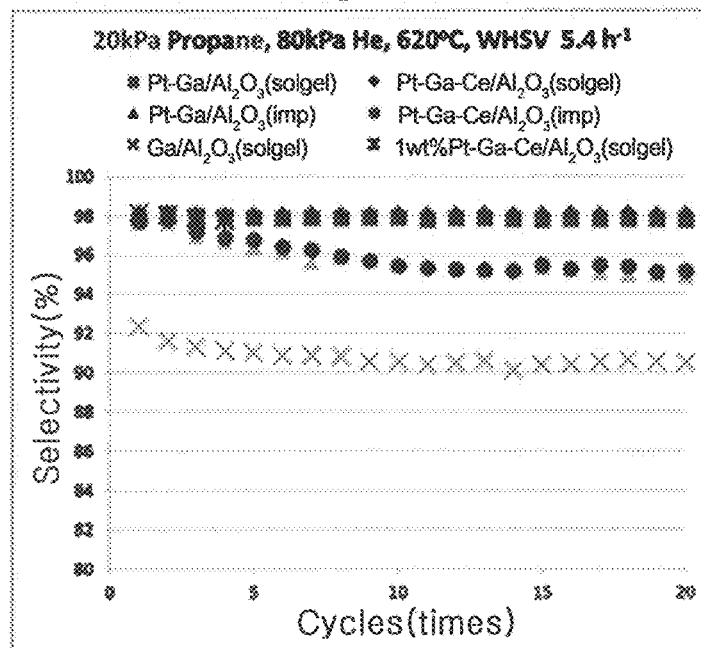
FIG. 3 is a graph showing the propylene selectivity during 20 cycles of propane dehydrogenation and catalyst regeneration in Example 1 of the present invention.

A total of 20 cycles of catalytic reaction/regeneration were performed. After 10 min from the reactant was introduced, propane conversion and propylene selectivity were analyzed using online GC. The propane dehydrogenation conversion and the propylene selectivity of the catalysts are shown in FIGS. 2 and 3. Based on the reaction results, the activity and regenerability of the Pt—Ga—Ce/Al$_2$O$_3$ (sol-gel) catalyst prepared through the addition of Ce and the use of a sol-gel process were the highest. Additionally, the propane dehydrogenation activity of the 1 wt % Pt—Ga—Ce/Al$_2$O$_3$ (sol-gel) in which the amount of Pt was increased to about 1 wt % was measured. The results are shown in FIGS. 2 and 3. In an embodiment of the present invention, Ga functions as the main active site, and thus the amount of Pt is particularly set to about 0.1 wt % based on the amount of alumina. In the case where the amount of Pt is increased to 1 wt %, as shown in FIGS. 2 and 3, the performance of the catalyst may deteriorate somewhat. In this way, the catalyst according to the present invention is featured in that appropriate amounts of the catalyst components are contained. In the catalyst according to an embodiment of the present invention, the activity of the 1% Pt catalyst is less than that of the 0.1% Pt catalyst, which indicates that the noble metal, namely Pt, is not the main active material.

Example 2

Measurement of Isobutane Dehydrogenation Reactivity

The four synthesized samples, that is, Pt—Ga/Al$_2$O$_3$ (imp), Pt—Ga—Ce/Al$_2$O$_3$ (imp), Pt—Ga/Al$_2$O$_3$ (sol-gel), and Pt—Ga—Ce/Al$_2$O$_3$ (sol-gel), were subjected to isobutane dehydrogenation/catalyst regeneration cycling.

Before the isobutane dehydrogenation, to minimize the effects of heat and material transfer, each sample was formed to a size of about 75 to about 100 meshes, and was used as a final catalyst for the reaction. The reaction was carried out using about 0.6 g of the catalyst in a fixed-bed continuous flow reactor, and all the samples were heated in-situ under conditions of about 823 K and a He flow rate of about 200 sccm, before reaction. The isobutane dehydrogenation was carried out under operating conditions of WHSV=7.1 hr$^{-1}$, 823 K, P$_{He}$=80 kPa, and P$_{isobutane}$=20 kPa. The reaction was carried out for about 1 hr, to followed by catalyst regeneration and then reaction. Specifically, reaction/catalyst regeneration cycling was performed as follows:

(i) performing primary isobutane dehydrogenation at about 823 K for about 1 hr;

(ii) allowing helium to flow at about 823 K for about 30 min;

(iii) regenerating the catalyst in dry air at about 823 K for about 30 min;

(iv) allowing helium to flow at about 823 K for about 30 min; and (v) performing secondary isobutane dehydrogenation at about 823 K.

Figure 4:
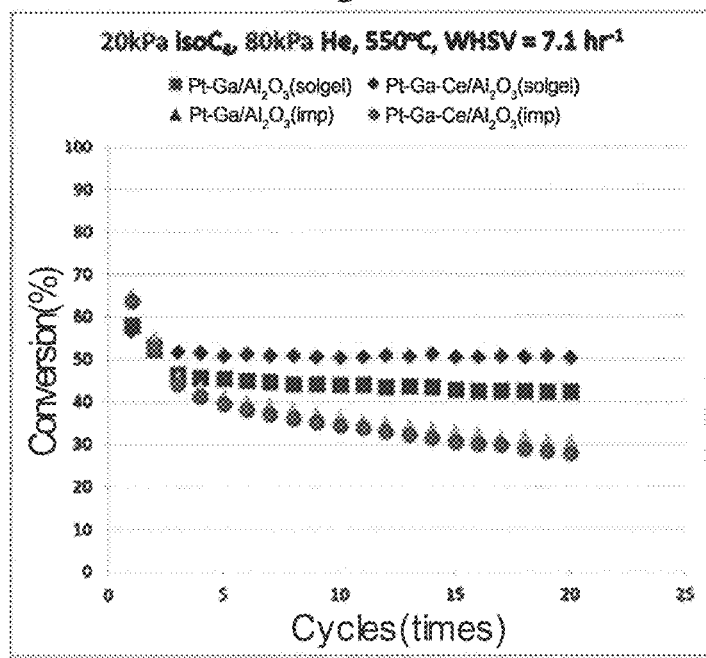
FIG. 4 is a graph showing the isobutane conversion during 20 cycles of isobutane dehydrogenation and catalyst regeneration in Example 2 of the present invention.
Figure 5:
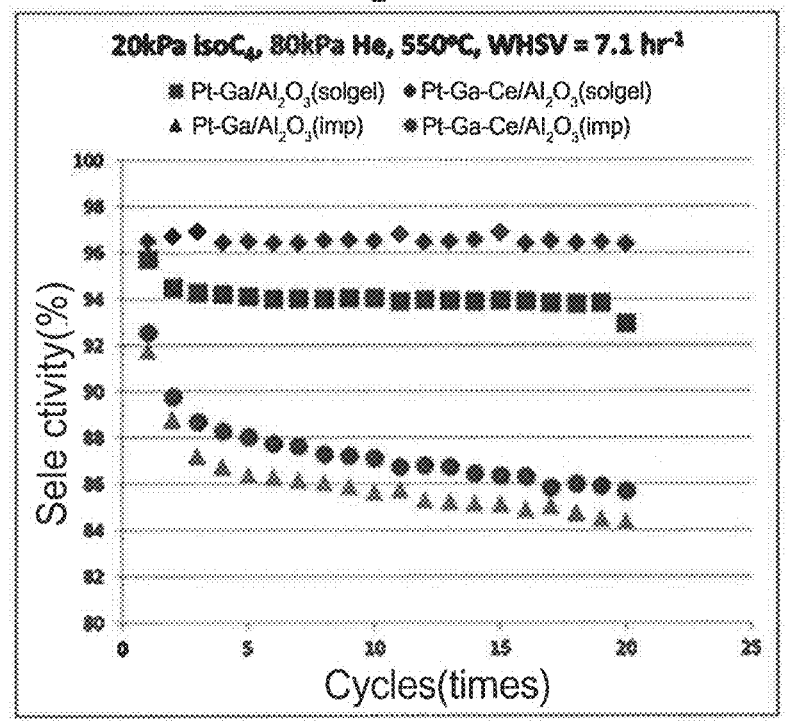
FIG. 5 is a graph showing the isobutylene selectivity during 20 cycles of isobutane dehydrogenation and catalyst regeneration in Example 2 of the present invention.

A total of 20 cycles of catalytic reaction/regeneration were performed. After 10 min from the reactant was introduced, isobutane conversion and isobutylene selectivity were analyzed using on-line GC. The isobutane dehydrogenation conversion and the isobutylene selectivity of the catalysts are shows FIGS. 4 and 5. Based on the reaction results, the activity and regenerability of the Pt—Ga—Ce/Al$_2$O$_3$ (sol-gel) catalyst prepared through the addition of Ce and the use of a sol-gel process were the greatest.

Example 3

Analysis of CO Chemisorption

In order to analyze the Pt dispersion exposed to the surface of the catalyst before and after the propane and isobutane dehydrogenation of Pt—Ga/Al$_2$O$_3$ (imp), Pt—Ga/Al$_2$O$_3$ (sol-gel) and Pt—Ga—Ce/Al$_2$O$_3$ (sol-gel) catalysts, CO chemisorption amount was measured (volumetric vacuum method) at about 323 K using ASAP2020 (Micromeritics). The results are shown in FIG. 6. Before the analysis of adsorption, all of the samples were reduced for about 3 hr while allowing H$_2$ to flow (about 100 sccm) at about 723 K, and were then treated in a vacuum at the same temperature for about 3 hr. Thereafter, the chemisorption amount was measured at about 323 K, which is the CO adsorption temperature. In order to increase the accuracy of analysis, analysis was performed five times per sample and the average value was taken. Based on the results of CO chemisorption, in the conventional Pt—Ga/Al$_2$O$_3$ (imp) synthesized using, incipient wetness impregnation, the Pt dispersion after propane dehydrogenation/catalyst regeneration cycling was remarkably decreased compared to the catalyst before the reaction. Meanwhile, in the Pt—Ga/Al$_2$O$_3$ (sol-gel) synthesized through one-pot mixing and a sol-gel process, the Pt dispersion after the reaction was maintained high, and in the Pt—Ga—Ce/Al$_2$O$_3$ (sol-gel) additionally having Ce, the Pt dispersion after the reaction was maintained higher. In the case of the isobutane dehydrogenation, the dispersion was not significantly decreased compared to the case of propane dehydrogenation, but the extent of maintaining the relative dispersion among the samples was similar to that of the propane dehydrogenation.

Example 4

TEM (Transmission Electron Microscopy)

The Pt—Ga/Al$_2$O$_3$ (imp) and Pt—Ga—Ce/Al$_2$O$_3$ (sol-gel) catalysts were subjected to a total of 20 cycles of propane dehydrogenation/regeneration or isobutane dehydrogenation/regeneration, after which TEM images thereof were analyzed. The results are shown in FIG. 7. As shown in the FIG. 7, the Pt cluster was dispersed in a smaller size after the reaction cycles in the Pt—Ga—Ce/Al$_2$O$_3$ (sol-gel) sample than in the Pt—Ga/Al$_2$O$_3$ (imp).

Example 5

Analysis of Pt L$_3$-Edge XANES (X-Ray Absorption Near-Edge Structure)

Figure 8:
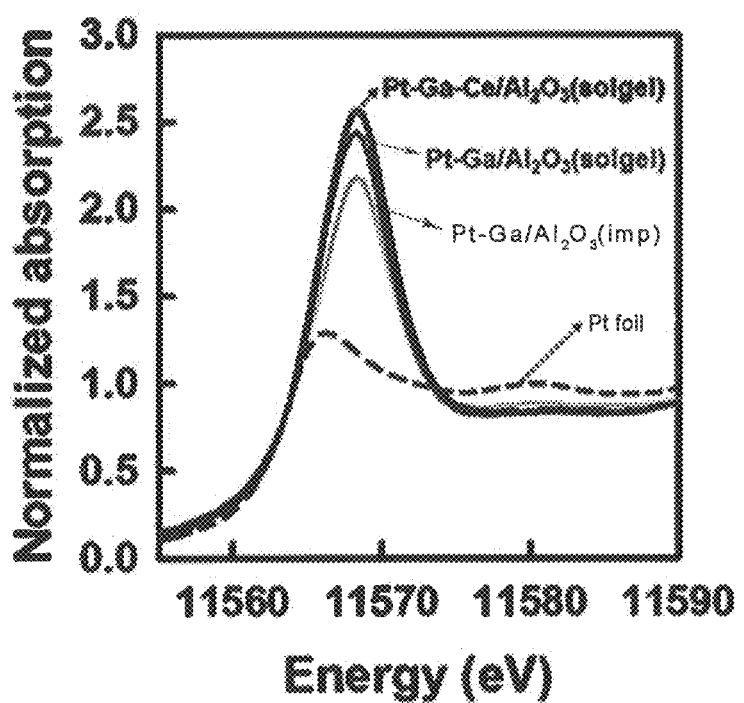
FIG. 8 is a graph showing the Pt $L_3$-edge XANES (X-ray Absorption Near-Edge Structure) spectra of the catalysts before reaction in Example 5 of the present invention.

The three kinds of synthesized catalysts, that is, Pt—Ga/Al$_2$O$_3$ (imp), Pt—Ga/Al$_2$O$_3$ (sol-gel), and Pt—Ga—Ce/Al$_2$O$_3$ (sol-gel), along with Pt foil as a reference catalyst, were subjected to Pt L$_3$-edge XANES analysis. The results are shown in FIG. 8. As shown in FIG. 8, the intensity of the white line at Pt L$_3$-edge absorption edge increased in the sequence of Pt—Ga/Al$_2$O$_3$ (imp), Pt—Ga/Al$_2$O$_3$ (sol-gel), and Pt—Ga—Ce/Al$_2$O$_3$ (sol-gel). Based on the results in which the intensity of the white line of Pt—Ga/Al$_2$O$_3$ (sol-gel) having the same chemical composition as Pt—Ga/Al$_2$O$_3$ (imp) is greater, Pt can be found to more strongly interact with alumina, which is deemed to be because Pt is surrounded by alumina and thus the interface between Pt and alumina is increased in the Pt—Ga/Al$_2$O$_3$ (sol-gel). Also, the intensity of the white line of Pt—Ga—Ce/Al$_2$O$_3$ (sol-gel) is the greatest, from which it can be concluded that Pt was more strongly stabilized.

Accordingly, simple modifications or variations of the present invention fall within the scope of the present invention as defined in the accompanying claims.

What is claimed is:

1. A method of preparing a complex oxide catalyst for dehydrogenation, comprising:
    providing a precursor of a first transition metal selected from the group consisting of gallium, vanadium, chromium, manganese, molybdenum, and zinc;
    providing a precursor of a hydrogen-activating metal comprising at least one selected from the group consisting of Groups 8, 9, 10, and 11 elements in a periodic table;
    providing an alumina precursor;
    mixing the precursor of the first transition metal, the precursor of the hydrogen-activating metal and the alumina precursor in one pot to obtain a mixture; and
    synthesizing a catalyst from the mixture in one pot using a sol-gel process, wherein the precursor of the first transition metal, the precursor of the hydrogen-activating metal and the alumina precursor are dissolved in a water, and stirred to hydrolyze the alumina precursor,
    wherein the amount of the first transition metal is 0.1 wt % to 20 wt % and the amount of the hydrogen-activating metal is 0.01 wt % to 2 wt %, based on an amount of alumina in a final catalyst.

2. The method of claim 1, further comprising:
    providing a precursor of a second transition metal selected from the group consisting of cerium and zirconium; and
    mixing the precursor of the second transition metal in the one pot, wherein the amount of the second transition metal is 0.1 wt % to 20 wt % based on the amount of the alumina in the final catalyst.

3. The method of claim 2, further comprising impregnating a hydrogen-activating metal comprising at least one selected from the group consisting of Groups 8, 9, 10, and 11 elements in a periodic table, after synthesizing the catalyst using the sol-gel process, wherein an amount of the hydrogen-activating metal is 0.01 wt % to 2 wt % based on the amount of the alumina in the final catalyst.

4. The method of claim 2, further comprising impregnating a second transition metal selected from the group consisting of cerium and zirconium, wherein an amount of the second transition metal is 0.1 wt % to 20 wt % based on the amount of the alumina in the final catalyst.

5. The method of claim 2, further comprising drying and thermally treating the catalyst, after synthesizing the catalyst using the sol-gel process.

6. The method of claim 5, wherein the drying is performed at a temperature of 50 to 200° C., and the thermally treating is performed at a temperature of 350 to 1000° C.

7. The method of claim 1, further comprising impregnating a second transition metal selected from the group consisting of cerium and zirconium, wherein an amount of the second transition metal is 0.1 wt % to 20 wt % based on the amount of the alumina in the final catalyst.

8. The method of claim 1, further comprising drying and thermally treating the catalyst, after synthesizing the catalyst using the sol-gel process.

9. The method of claim 8, wherein the drying is performed at a temperature of 50 to 200° C., and the thermally treating is performed at a temperature of 350 to 1000° C.

10. The method of claim 1, wherein the hydrogen-activating metal comprises at least one selected from the group consisting of Co, Ni, Cu, Ru, Rh, Pd, Ag, Ir, Pt and Au.

11. The method of claim 1, further comprising impregnating a hydrogen-activating metal comprising at least one selected from the group consisting of Groups 8, 9, 10, and 11 elements in a periodic table, after synthesizing the catalyst using the sol-gel process, wherein an amount of the hydrogen-activating metal is 0.01 wt% to 2 wt% based on the amount of the alumina in the final catalyst.

* * * * *